(12) United States Patent
Conway

(10) Patent No.: US 11,287,212 B2
(45) Date of Patent: Mar. 29, 2022

(54) RECOIL PAD WITH SURVIVAL MODULE KIT

(71) Applicant: Ernest Lee Conway, Denver, CO (US)

(72) Inventor: Ernest Lee Conway, Denver, CO (US)

( * ) Notice: Subject to any disclaimer, the term of this patent is extended or adjusted under 35 U.S.C. 154(b) by 0 days.

(21) Appl. No.: 17/064,302

(22) Filed: Oct. 6, 2020

(65) Prior Publication Data
US 2021/0247162 A1 Aug. 12, 2021

Related U.S. Application Data

(60) Provisional application No. 62/971,970, filed on Feb. 8, 2020.

(51) Int. Cl.
*F41C 23/08* (2006.01)
*F41C 23/20* (2006.01)
*A61F 17/00* (2006.01)

(52) U.S. Cl.
CPC .............. *F41C 23/08* (2013.01); *A61F 17/00* (2013.01); *F41C 23/20* (2013.01)

(58) Field of Classification Search
CPC .......... F41C 23/08; F41C 23/20; F41C 23/22; F41C 27/00
See application file for complete search history.

(56) References Cited

U.S. PATENT DOCUMENTS

| | | | | |
|---|---|---|---|---|
| 2,468,349 A | * | 4/1949 | Stewart | F41C 23/08 42/74 |
| 3,696,544 A | * | 10/1972 | Webb | F41C 23/08 42/74 |
| 4,697,367 A | | 10/1987 | Brophy | |
| 4,769,937 A | | 9/1988 | Gregory | |
| 5,048,213 A | | 9/1991 | Gerhard | |
| 5,068,991 A | * | 12/1991 | Reed | F41C 23/22 42/71.01 |

(Continued)

FOREIGN PATENT DOCUMENTS

| | | | | |
|---|---|---|---|---|
| DE | | 867509 C | * 2/1953 | ............. F41C 27/00 |
| WO | WO2008097308 | | 8/2008 | |

OTHER PUBLICATIONS

Shotgun Stock Survival Kit. <https://www.instructables.com/Shotgun-Stock-Survival-Kit/>. 2015. (Year: 2015).*

(Continued)

*Primary Examiner* — Gabriel J. Klein
(74) *Attorney, Agent, or Firm* — Stanley J. Gradisar Attorney At Law, LLC; Stanley J. Gradisar

(57) ABSTRACT

A recoil pad with survival module kit provides rifle recoil absorption and also provides peace of mind to a hunter as a means of carrying essential survival components in a compact form in a way which currently is not provided in the art. In a hunting situation in the wilds, the loss of backpacks or other means of carrying a first aid kit can arise. The most important thing a hunter will try to avoid losing is his or her rifle. Thus, the recoil pad with survival module kit will always be available to the hunter if a crucial scenario should occur as long as the hunter retains the rifle. The survival module kit is compressible within the recoil pad and provides the same recoil absorption as currently available recoil pads along with the added convenience of all of the items contained in the survival module kit.

12 Claims, 7 Drawing Sheets

(56) References Cited

U.S. PATENT DOCUMENTS

| | | |
|---|---|---|
| 52,265,613 | 7/1993 | Claridge |
| 5,634,289 A * | 6/1997 | Wascher ................. F41C 23/02 |
| | | 42/104 |
| 5,924,233 A | 7/1999 | Strobel |
| 6,536,152 B1 | 3/2003 | Wisz |
| 6,640,480 B2 | 11/2003 | Williams |
| 6,829,855 B2 | 12/2004 | Seifert |
| 7,637,049 B1 | 12/2009 | Samson |
| 8,327,568 B1 | 12/2012 | Lavergne |
| 9,827,433 B2 | 11/2017 | Wu |
| 10,247,513 B1 | 4/2019 | Goldense |

OTHER PUBLICATIONS

Survive-It. Advantages of Vacuum Packed Survival Kits for Workplaces. <https://survive-it.co.nz/2017/06/12/advantages-of-vacuum-packed-survival-kits-for-workplaces/>. Jun. 12, 2017 (Year: 2017).*
TOURBON Genuine Leather Shotgun Gun Butt Extension Recoil Pad—Small Size; Retrieved Apr. 15, 2019 from: https://www.amazon.com/TOURBON-Genuine-Leather-Shotgun-Extension/dp/B011A0EA9U/ref=sr_1_50?qid=1555338425&s=sports-and-fitness&sr=1-50.

* cited by examiner

RECOIL PAD WITH SURVIVAL MODULE KIT

CROSS-REFERENCES TO RELATED APPLICATIONS

This application claims the benefit of U.S. Provisional Application Ser. No. 62/971,970 filed on Feb. 8, 2020 and titled "RECOIL PAD WITH SURVIVAL MODULE KIT" which is incorporated herein by reference in its entirety for all that is taught and disclosed therein.

BACKGROUND OF THE INVENTION

The present invention relates to the general field of hunting with a rifle and to the particular field of rifle recoil pads. There are previously no known recoil pads which typically are constructed either as a one-piece molded rubber pad that incorporates a sleeve and recoil absorber that slips over the rifle's butt stock. Another example combines a neoprene sleeve with several different thickness foam pad inserts. Both designs absorb the recoil effect once a rifle is discharged.

SUMMARY OF THE INVENTION

This summary is provided to introduce in a condensed form concepts that are further explained in the detailed description. In the present state of the art there are no recoil pads that provide recoil absorption along with an incorporated survival module kit that is carried easily and provides the same recoil absorption along with additional safety and survival items essential to human life if a medical or survival situation arises. Heretofore safety and survival items had to be carried separately from the hunting rifle. The detailed description below outlines and describes a unique and improved recoil pad in combination with an emergency medical and survival kit incorporated as one unit. This combination provides hunters with an alternative way to have essential medical items and survival items on an as needed basis without additional weight or bulk.

Figure 1:
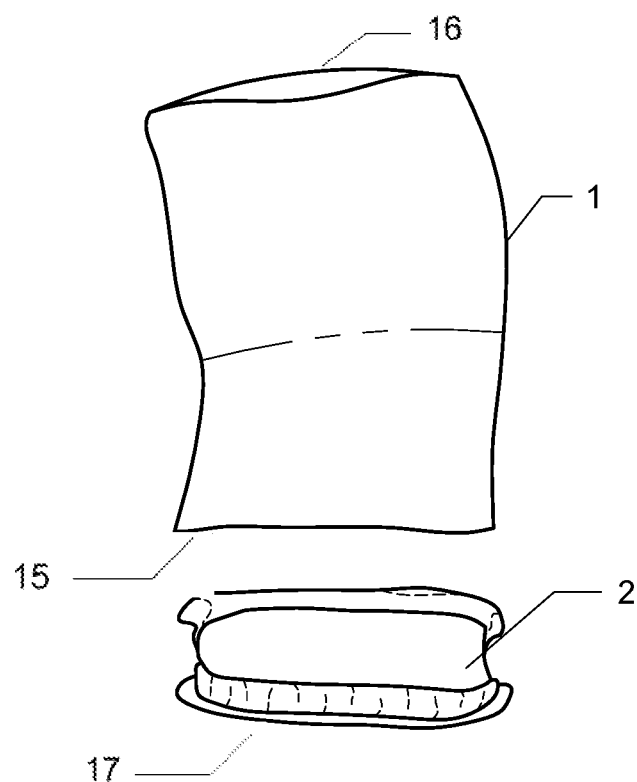
FIG. 1 shows a plan view of a stretchable slip-on sleeve with survival module insert in an embodiment of the present invention.

To assist in the understanding of the present disclosure the following list of components and associated numbering found in the drawings is provided herein:

| Table of Components | |
|---|---|
| Component | # |
| stretchable slip-on sleeve | 1 |
| survival module insert | 2 |
| packaged and vacuum sealed sterile 4" × 12' cotton gauze bandage | 3 |
| packaged and sealed sterile 2" × 3" non-stick gauze pad | 4 |
| packaged and sealed sterile medium size flex bandage | 5 |
| packaged and sealed sterile fingertip bandage | 6 |
| packaged and sealed sterile butterfly closure | 7 |
| 1" × 4" plastic brace/medical tape dispenser | 8 |
| ½" × 4' adhesive medical tape | 9 |
| packaged and vacuum sealed sterile 4" × 5' rolled cotton gauze | 10 |
| 10' length braided para-chord | 11 |
| 1" × 4" pressed cardboard support base and fire starter | 12 |
| gun stock | 13 |
| butt | 14 |
| open end | 15 |
| closed end | 16 |
| vacuum sealed plastic casing | 17 |

DETAILED DESCRIPTION

Referring now to the Figures, in which like reference numerals refer to structurally and/or functionally similar elements thereof, FIG. 1 shows a plan view of the stretchable slip-on sleeve 1 that has an open end 15 and a closed end 16. Stretchable slip-on sleeve 1 material may be made of neoprene, natural rubber, or types of synthetic rubber, or any other material that is both stretchable and durable.

Referring again to FIG. 1, also shown is the survival module insert 2 which contains one or more of the items listed in FIGS. 3-12 in an embodiment of the present invention. The survival module insert 2 is inserted all the way to abut against the closed end 16 of the stretchable slip-on sleeve 1. The open end 15 is then slid over the butt 14 of the gun stock 13 of a rifle until the butt 13, now inside of the stretchable slip-on sleeve 1, abuts against the survival module insert 2. The survival module insert 2 is compressible and absorbs the recoil effect when the rifle is discharged. A size of the stretchable slip-on sleeve 1 is such that the open end 15 slips snugly over the butt 14 of a gun stock 13 (see FIG. 13). Stretchable slip-on sleeve 1 is sized so that it will stay secure to the butt 14 of a gun stock 13 in normal use, but can be removed without difficulty when needed to access the survival module insert 2 contained therein. The stretchable slip-on sleeve 1 is manufactured in different sizes to snugly fit various sizes of butts of gun stocks. The survival module insert 2 is also sized to match the size of the stretchable slip-on sleeve 1.

Figure 2:
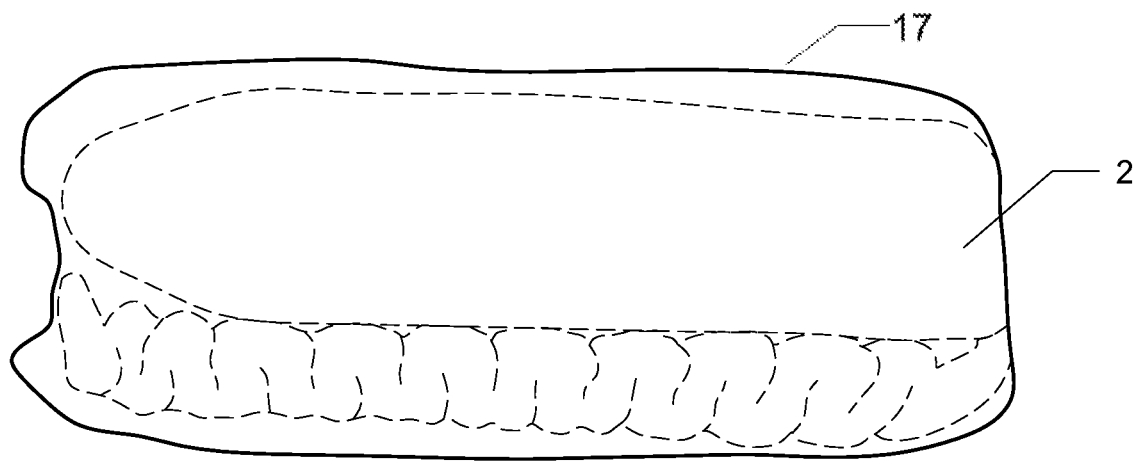
FIG. 2 shows an enlarged plan view of the survival module insert in an embodiment of the present invention.

FIG. 2 shows a plan view of the survival module insert 2 which is contained in a vacuum sealed plastic casing 17 in which the items shown in FIGS. 3-12 are assembled together. There is no particular order in which to assemble the items as long as the items are assembled together in a reasonably compact form. Vacuum sealed plastic casing 17 may be clear or opaque.

Figure 3:
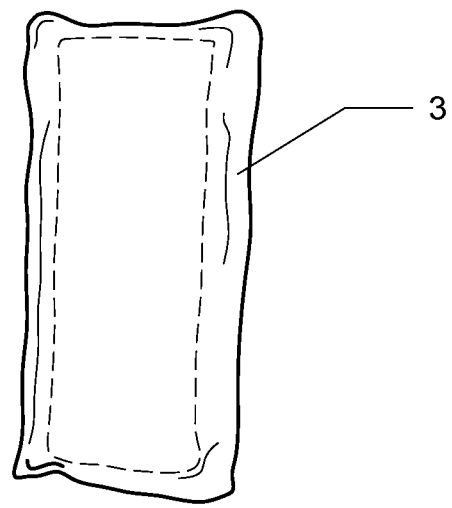
FIG. 3 shows a plan view of the packaged and vacuum sealed sterile 4"×12" cotton gauze bandage in an embodiment of the present invention.

FIG. 3 shows a plan view of the packaged and vacuum sealed sterile 4"×12' cotton bandage 3. Referring now to FIG. 3, packaged and vacuum sealed sterile 4"×12' cotton bandage 3 is a thin woven fabric that is placed over a wound to protect and keep it clean so air can penetrate and improve healing. It also prevents excess moisture around the wound site. It can also be used as a temporary sling for support of injured limbs. It also can provide a multitude of other uses in emergency survival situations. One or more of packaged and vacuum sealed sterile 4"×12' cotton bandages 3 may be included in the survival module insert 2.

Figure 4:
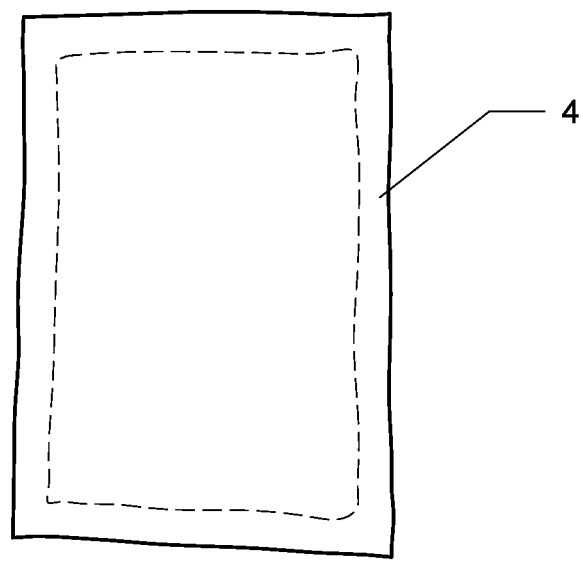
FIG. 4 shows a plan view of the packaged and sealed sterile 2"×3" non-stick gauze pad in an embodiment of the present invention.

FIG. 4 shows a plan view of the packaged and sealed sterile 2"×3" non-stick gauze pad 4. Referring now to FIG. 4, packaged and sealed sterile 2"×3" non-stick gauze pad 4 keeps wounds clean, dry, and protected. It provides non-stick contact with wounds while allowing fluids to be absorbed. It is typically used over surgical sites, scrapes, and burns, and to prevent trauma during dressing changes. It also can provide a multitude of other uses in emergency survival situations. One or more of packaged and sealed sterile 2"×3" non-stick gauze pads 4 may be included in the survival module insert 2.

Figure 5:
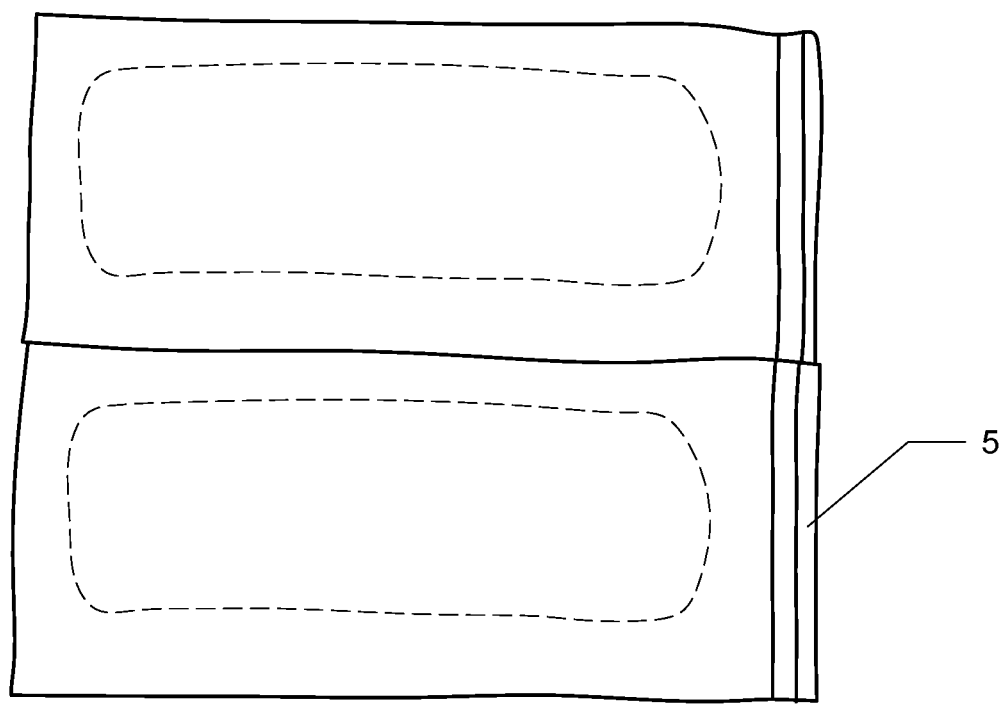
FIG. 5 shows a plan view of the packaged and sealed sterile medium size flex bandages in an embodiment of the present invention.

FIG. 5 shows a plan view of the packaged and sealed sterile medium size flex bandage 5. Referring now to FIG. 5, packaged and sealed sterile medium size flex bandage 5 is used for covering of wounds to protect against dirt and germs that may cause infection. It also can provide a multitude of other uses in emergency survival situations. One or more of packaged and sealed sterile medium size flex bandages 5 may be included in the survival module insert 2.

Figure 6:
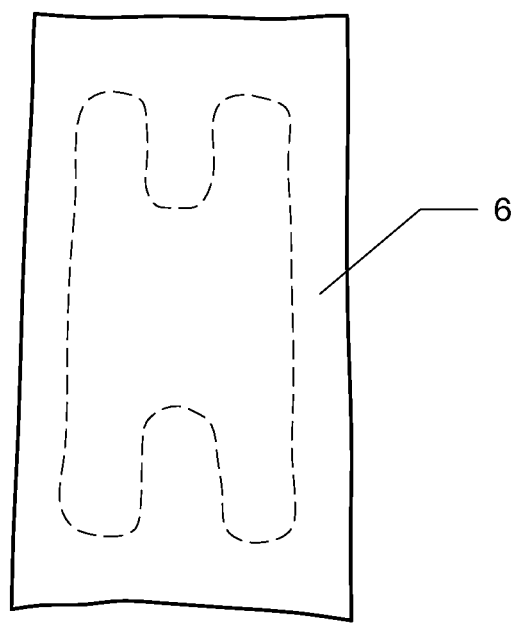
FIG. 6 shows a plan view of the packaged and sealed sterile fingertip bandages in an embodiment of the present invention.

FIG. 6 shows a plan view of the packaged and sealed sterile fingertip bandage 6. Referring now to FIG. 6, packaged and sealed sterile fingertip bandage 6 is a butterfly shaped adhesive strip. It is ready to use for dressing minor cuts, abrasions, and puncture wounds over fingertips and toes. It is non-stick to absorb fluids and cushion wounds. It also can provide a multitude of other uses in emergency survival situations. One or more of packaged and sealed sterile fingertip bandages 6 may be included in the survival module insert 2.

Figure 7:
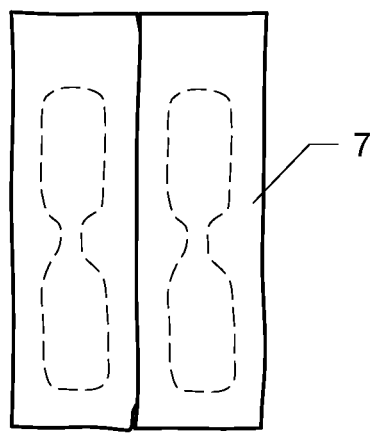
FIG. 7 shows a plan view the packaged and sealed sterile butterfly closure in an embodiment of the present invention.

FIG. 7 shows a plan view of the packaged and sealed sterile butterfly closure 7. Referring now to FIG. 7, packaged and sealed sterile butterfly closures 7 are a thin adhesive strip used to close small wounds which are applied across the laceration and then pulls the skin on either side of the wound together. It can also provide a multitude of other uses in emergency survival situations. One or more of packaged and sealed sterile butterfly closures 7 may be included in the survival module insert 2.

Figure 8:
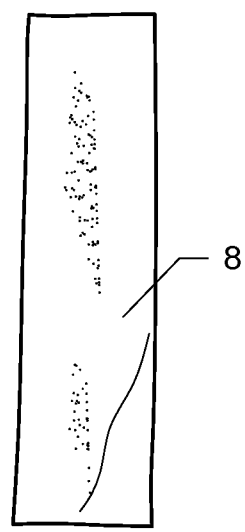
FIG. 8 shows a plan view of the 1"×4" plastic brace and medical tape dispenser in an embodiment of the present invention.

FIG. 8 shows a plan view of the 1"×4" plastic brace/medical tape dispenser 8. Referring now to FIG. 8, 1"×4" plastic brace/medical tape dispenser 8 is used for additional support for the survival module insert 2 as well as a means for wrapping the adhesive medical tape 9 (shown in FIG. 9) around it. 1"×4" plastic brace/medical tape dispenser 8 can also be used to support broken fingers. It can also provide a multitude of other uses in emergency survival situations. One or more of 1"×4" plastic brace/medical tape dispensers 8 may be included in the survival module insert 2.

Figure 9:
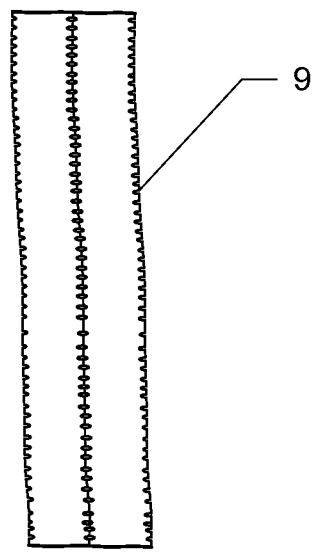
FIG. 9 shows a plan view of the ½"×4' adhesive medical tape that can be wrapped around the plastic brace and medical tape dispenser of FIG. 8 in an embodiment of the present invention.

FIG. 9 shows a plan view of the ½"×4' adhesive medical tape 9 which can be wrapped around the 1"×4" plastic brace and medical tape dispenser shown in FIG. 8. Referring now to FIG. 8, ½"×4' adhesive medical tape 9 is primarily used along with gauze-type bandages to protect wounds and scrapes from friction, bacteria, damage, and dirt. It holds wound bandages or other first aid or medical appliances in place. It can also provide a multitude of other uses in emergency survival situations. One or more of ½"×4' adhesive medical tapes 9 may be included in the survival module insert 2.

Figure 10:
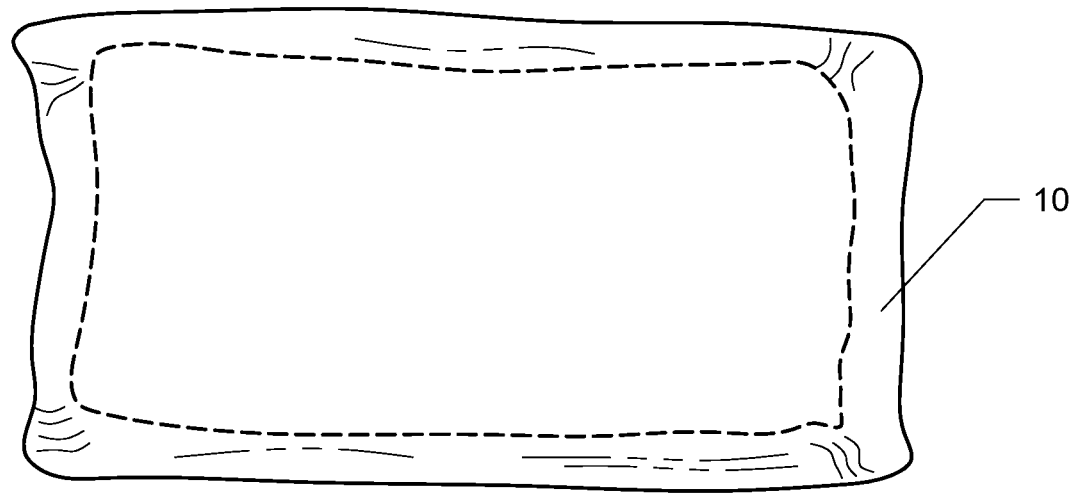
FIG. 10 shows a plan view of the packaged and vacuum sealed sterile 4"×5' rolled cotton gauze in an embodiment of the present invention.

FIG. 10 shows a plan view of the packaged and vacuum sealed sterile 4"×5' rolled cotton gauze 10. Referring now to FIG. 10, packaged and vacuum sealed sterile 4"×5' rolled cotton gauze 10 is primarily used as a means of affixing a field dressing over a wound. It is also used to absorb any exudate that makes it through the first layer of the wound dressing. It can also provide a multitude of other uses in emergency survival situations. One or more of packaged and vacuum sealed sterile 4"×5' rolled cotton gauzes 10 may be included in the survival module insert 2.

Figure 11:
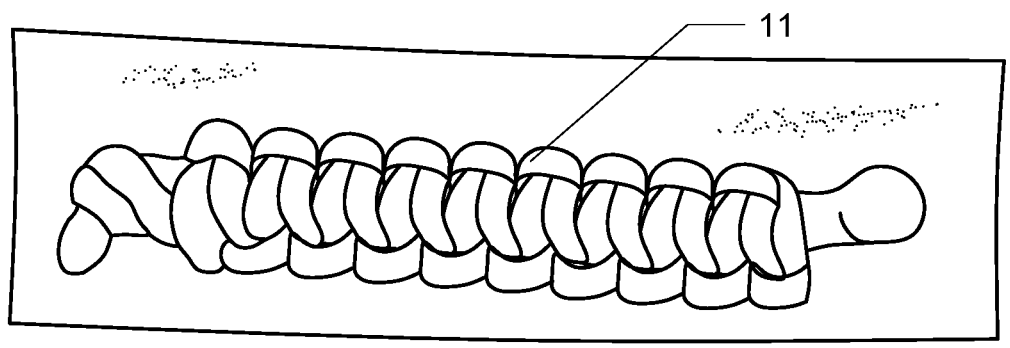
FIG. 11 shows a plan view of the 10' braided length of para-cord in an embodiment of the present invention.

FIG. 11 shows a plan view of the 10' length braided para-cord 11 which is braided for ease of packaging in the survival module insert 2. Referring now to FIG. 11, the 10' length braided para-cord 11 can be used as a lanyard, snare, laces, bow drill, clothing repair, belt, sling, cordage, trail marking, emergency tourniquet, shelter making, and splints. It can also provide a multitude of other uses in emergency survival situations. One or more of the 10' length braided para-cords 11 may be included in the survival module insert 2.

Figure 12:
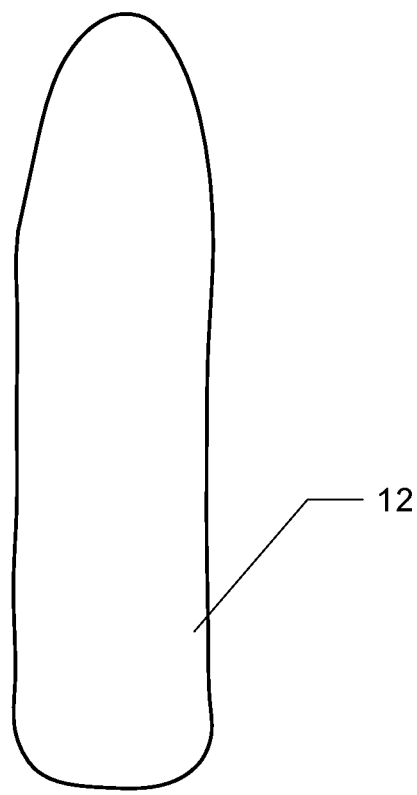
FIG. 12 shows a plan view of the 1"×4" piece of pressed cardboard support brace and fire starter in an embodiment of the present invention.

FIG. 12 shows a plan view of the 1"×4" pressed cardboard support base and fire starter 12. Referring now to FIG. 12, the 1"×4" pressed cardboard support base and fire starter 12 is primarily used for added support of the survival module insert 2 to keep its uniform shape when inserted into the stretchable slip-on sleeve 1. When shredded it is an excellent means as a fire starter. It can also provide a multitude of other uses in emergency survival situations. One or more of the 1"×4" pressed cardboard support base and fire starters 12 may be included in the survival module insert 2.

The individual items shown in FIGS. 3-12 are illustrative of the types of medical supplies that could be included in the survival module insert 2 and are not considered to be limited to only these items disclosed. Various combinations of the items disclosed, plus other medical supplies not specifically disclosed, may be packaged together in the survival module insert 2 to meet specific needs or requirements.

Figure 13:
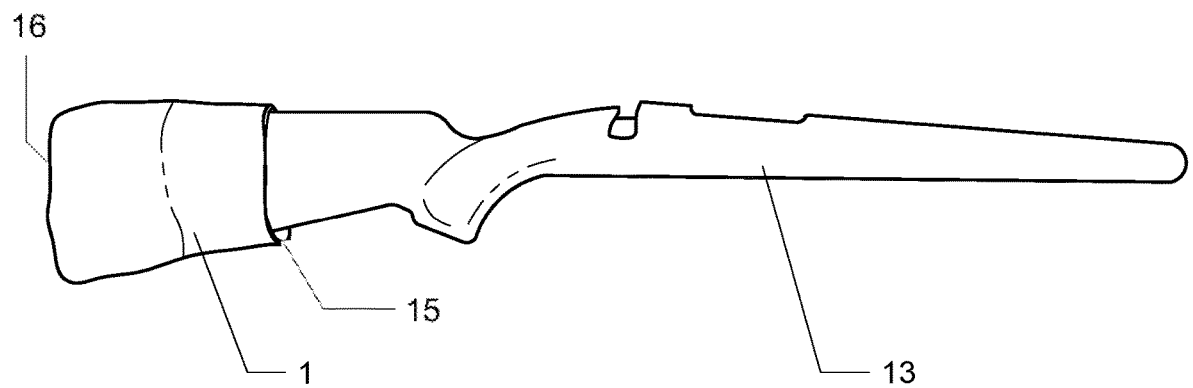
FIG. 13 shows plan view of a stretchable slip-on sleeve with survival module insert inside slipped onto a rifle stock in an embodiment of the present invention.

FIG. 13 shows plan view of a stretchable slip-on sleeve with survival module insert inside slipped onto a gun stock in an embodiment of the present invention. Referring now to FIG. 13, the gun stock 13 is shown with the stretchable slip-on sleeve 1 slipped on to the butt 14 of gun stock 13. The survival module insert 2 has already been inserted into the closed end of the stretchable slip-on sleeve 1 and is not visible.

Figure 14:
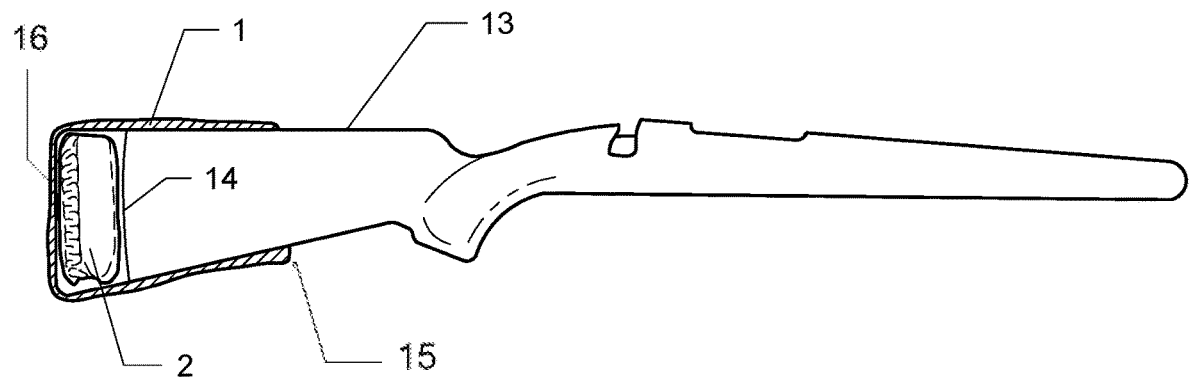
FIG. 14 shows a plan view and a cross-section view of a stretchable slip-on sleeve with survival module insert inside slipped onto a rifle stock in an embodiment of the present invention.

FIG. 14 shows a plan view and a cross-section view of a stretchable slip-on sleeve with survival module insert inside slipped onto a rifle stock in an embodiment of the present invention. Referring now to FIG. 14, the top half of the stretchable slip-on sleeve 1 is shown removed to reveal the survival module insert 2 at the closed end of the stretchable slip-on sleeve 1 and butted up against the butt 14 of gun stock 13.

Having described the present invention, it will be understood by those skilled in the art that many changes in construction and widely differing embodiments and applications of the invention will suggest themselves without departing from the scope of the present invention.

What is claimed is:

1. A recoil pad comprising:
   a stretchable slip-on sleeve having an open end and a closed end; and
   a compressible survival module insert inserted into the open end of the stretchable slip-on sleeve and abutting against the closed end of the stretchable slip-on sleeve, the compressible survival module insert containing within itself:
   at least one medical item and
   at least one survival item; and wherein the compressible survival module insert is configured to provide recoil absorption when the stretchable slip-on sleeve is positioned over a butt of a gun stock.

2. The recoil pad according to claim 1 further comprising:
   a vacuum sealed plastic casing containing the survival module insert.

3. The recoil pad according to claim 1 further comprising:
   a size of the stretchable slip-on sleeve configured to enable the open end to be slipped snugly onto the butt of a gun stock.

4. The recoil pad according to claim 1 wherein the at least one medical item is selected from the group consisting of:
   a cotton gauze bandage;
   a non-stick gauze pad;
   a flex bandage;
   a fingertip bandage;
   a butterfly closure;
   a plastic brace and/or medical tape dispenser;
   an adhesive medical tape; and
   a rolled cotton gauze.

5. The recoil pad according to claim 1 wherein the at least one survival item is selected from the group consisting of:
   a para-cord; and
   a pressed cardboard support base and fire starter.

6. The recoil pad according to claim 1 wherein the stretchable slip-on sleeve is made from a material selected from the group consisting of:
   a neoprene;
   a natural rubber;
   a synthetic rubber; and
   a material that is both stretchable and durable.

7. A method comprising the steps of:
   (a) assembling a survival module insert with at least one medical item and at least one survival item;
   (b) sizing a stretchable slip-on sleeve having a closed end and an open end;
   (c) inserting the survival module insert through the open end of the stretchable slip-on sleeve;
   (d) abutting the survival module insert against the closed end of the stretchable slip-on sleeve;
   (e) sliding the open end of the stretchable slip-on sleeve over the butt of a gun stock of a rifle until the butt of the gun stock abuts against the survival module insert; wherein the survival module insert is compressible and absorbs a recoil effect when the rifle is discharged.

8. The method according to claim 7 wherein assembling step (a) further comprises the step of:
   assembling the at least one medical item and at least one survival item in a compact form suitable to the inserting step (c).

9. The method according to claim 7 wherein assembling step (a) further comprises the step of:
   selecting the at least one medical item from the group consisting of:
   a cotton gauze bandage;
   a non-stick gauze pad;
   a flex bandage;
   a fingertip bandage;
   a butterfly closure;
   a plastic brace and/or medical tape dispenser;
   an adhesive medical tape; and
   a rolled cotton gauze.

10. The method according to claim 7 wherein assembling step (a) further comprises the step of:
    selecting the at least one survival item from the group consisting of:
    a para-cord; and
    a pressed cardboard support base and fire starter.

11. The method according to claim 7 wherein assembling step (a) further comprises the step of:
    encasing the stretchable slip-on sleeve in a vacuum sealed plastic casing.

12. The method according to claim 7 further comprising the step of:
    making the stretchable slip-on sleeve from a material selected from the group consisting of:
    a neoprene;
    a natural rubber;
    a synthetic rubber; and
    a material that is both stretchable and durable.

* * * * *